United States Patent
Yoneda et al.

(10) Patent No.: US 8,227,267 B2
(45) Date of Patent: Jul. 24, 2012

(54) TEMPLATE INSPECTION METHOD AND MANUFACTURING METHOD FOR SEMICONDUCTOR DEVICE

(75) Inventors: Ikuo Yoneda, Kanagawa (JP); Tetsuro Nakasugi, Kanagawa (JP); Masamitsu Itoh, Kanagawa (JP); Ryoichi Inanami, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 387 days.

(21) Appl. No.: 12/553,906

(22) Filed: Sep. 3, 2009

(65) Prior Publication Data

US 2010/0075443 A1    Mar. 25, 2010

(30) Foreign Application Priority Data

Sep. 25, 2008  (JP) .................. 2008-245559

(51) Int. Cl.
*H01L 21/66* (2006.01)

(52) U.S. Cl. ...................... 438/16; 438/14; 382/144

(58) Field of Classification Search .............. 438/14, 438/16; 257/E21.53; 430/30; 382/144; 702/35; 356/237.1
See application file for complete search history.

(56) References Cited

U.S. PATENT DOCUMENTS

| 7,440,092 B2 | 10/2008 | Shibata et al. |
| 2002/0093122 A1 | 7/2002 | Choi et al. |
| 2003/0205658 A1 | 11/2003 | Voisin |
| 2010/0075443 A1* | 3/2010 | Yoneda et al. ............ 438/16 |
| 2010/0237045 A1* | 9/2010 | Koshiba et al. ............ 216/48 |

FOREIGN PATENT DOCUMENTS

| JP | 2000-194142 | 7/2000 |
| JP | 2001-68411 | 3/2001 |
| JP | 2005-83800 | 3/2005 |
| JP | 2008-134214 | 6/2008 |

OTHER PUBLICATIONS

Notice of Rejection issued by the Japanese Patent Office on Oct. 19, 2010, for Japanese Patent Application No. 2008-245559, and English-language translation thereof.

* cited by examiner

*Primary Examiner* — Jack Chen

(74) *Attorney, Agent, or Firm* — Finnegan, Henderson, Farabow, Garrett & Dunner, L.L.P.

(57) ABSTRACT

A template inspection method for performing defect inspection of a template, by bringing a pattern formation surface of a template used to form a pattern close to a first fluid coated on a flat substrate, filling the first fluid into a pattern of the template, and by performing optical observation of the template in a state that the first fluid is sandwiched between the template and the substrate, wherein a difference between an optical constant of the first fluid and an optical constant of the template is larger than a difference between an optical constant of air and the optical constant of the template.

8 Claims, 7 Drawing Sheets

TEMPLATE INSPECTION METHOD AND MANUFACTURING METHOD FOR SEMICONDUCTOR DEVICE

CROSS-REFERENCE TO RELATED APPLICATIONS

This application is based upon and claims the benefit of priority from the prior Japanese Patent Application No. 2008-245559, filed on Sep. 25, 2008; the entire contents of which are incorporated herein by reference.

BACKGROUND OF THE INVENTION

1. Field of the Invention

The present invention relates to a template inspection method, and a manufacturing method for a semiconductor device.

2. Description of the Related Art

In a manufacturing process of semiconductor devices, attention has been paid on an optical imprint method for transferring a pattern of an original plate onto a substrate to which the pattern is to be transferred, as a technique of achieving both forming a fine pattern equal to or smaller than 100 nanometers and mass production of devices, for example. This optical imprint method transfers a pattern onto a light-curing organic-material layer (resist layer) coated on a substrate such as a wafer, by contacting to the resist layer a template formed with a pattern to be transferred, and by curing the resist layer by irradiating light in this state (for example, see Japanese Patent Application Laid-open No. 2001-68411 and Japanese Patent Application Laid-open No. 2000-194142).

Particularly, the optical imprint method is most expected to be applied to semiconductor lithography. The imprint has characteristics such that it uses a template of the same magnification and it is a contacting process with an organic material. Therefore, defect management of imprint has been difficult. Particularly, defect inspection of a template is believed to be one of the most important research issues of imprint.

BRIEF SUMMARY OF THE INVENTION

According to an aspect of the present invention, there is provided a template inspection method for performing defect inspection of a template, by bringing a pattern formation surface of a template used to form a pattern close to a first fluid coated on a flat substrate, filling the first fluid into a pattern of the template, and by performing optical observation of the template in a state that the first fluid is sandwiched between the template and the substrate, wherein a difference between an optical constant of the first fluid and an optical constant of the template is larger than a difference between an optical constant of air and the optical constant of the template.

According to an aspect of the present invention, there is provided a template inspection method for performing defect inspection of a template, by bringing a pattern formation surface of a template used to form a pattern close to a first fluid coated on a flat substrate, filling the first fluid into a pattern of the template, and by performing optical observation of the template in a state that the first fluid is sandwiched between the template and the substrate, wherein an optical constant of the first fluid is the same as an optical constant of the template.

According to an aspect of the present invention, there is provided a template inspection method for performing defect inspection of a template, by bringing a pattern formation surface of the template used to form a pattern close to a conductive light-curing material coated on a flat substrate, filling the conductive light-curing material into a pattern of the template, irradiating light to the conductive light-curing material in a state that the conductive light-curing material is sandwiched between the template and the substrate, thereby hardening the conductive light-curing material and transferring the pattern of the template to the conductive light-curing material, and by performing electron beam observation of a transfer pattern of the conductive light-curing material.

According to an aspect of the present invention, there is provided a manufacturing method for a semiconductor device, by bringing a pattern formation surface of a template used to form a pattern close to a first fluid coated on a flat first substrate, filling the first fluid into a pattern of the template, performing defect inspection of the template by performing optical observation of the template in a state that the first fluid is sandwiched between the template and the first substrate and a difference of an optical constant between the first fluid and the template is larger than a difference of the optical constant between air and the template, bringing a template which is confirmed to have no defect into contact with a curable material layer coated on a second substrate, and by forming a pattern on the second substrate by curing the curable material layer.

DETAILED DESCRIPTION OF THE INVENTION

Exemplary embodiments of a template inspection method, and a manufacturing method for a semiconductor device according to the present invention will be explained below in detail with reference to the accompanying drawings. The present invention is not limited to the embodiments.

Figure 1:
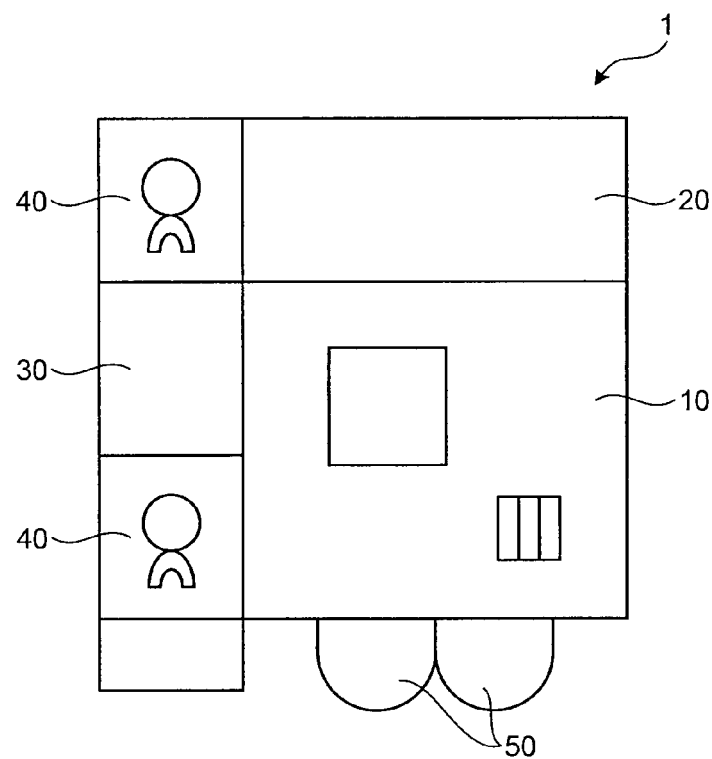
FIG. 1 is a configuration diagram of a template inspection apparatus according to a first embodiment of the present invention.

FIG. 1 is a configuration diagram of a template inspection apparatus according to a first embodiment of the present invention. FIG. 1 is a plan view of a template inspection apparatus (defect inspection apparatus) 1. The template inspection apparatus 1 performs defect inspection of a template (substrate to be inspected) used for an optical imprint-lithography method (hereinafter, "imprint"). The imprint is a method of microfabricating semiconductor devices and the like by transferring a pattern of an organic material (imprint resist) by contacting a patterned template to a substrate to which the pattern is to be transferred or by shortening a distance between the template and the substrate. Specifically, in the imprint, the template is contacted to a light-curing organic-material layer (resist layer) coated on a substrate such as a wafer, and light is irradiated thereto in this state to cure the resist layer, thereby transferring the pattern onto the resist layer.

The template inspection apparatus 1 according to the first embodiment performs defect inspection of a template by optically observing the template in a state that a fluid having a predetermined optical coefficient is sandwiched between a substrate such as a silicon wafer and the template. In the first embodiment, a fluid (fluid having an optical constant adjusted) of an optical constant corresponding to an optical constant and the like of the template is used. For the fluid, there is used a fluid of an optical constant having a large constant between an image of a template defect and an image of a template pattern when a defect inspection image of the template is captured.

The template inspection apparatus 1 includes an inspection-image acquisition mechanism (fluid coating unit, inspection optical unit) 10, an inspection-image processing mechanism (defect analyzing unit) 20, a template cleaning mechanism 30, a template station 40, and a wafer station 50.

The inspection-image acquisition mechanism 10 forms a pattern on a substrate (a substrate to which the pattern is to be transferred) such as a silicon wafer by imprint, and captures a defect inspection image of a template used for the imprint. The inspection-image acquisition mechanism 10 coats a imprint resist onto the substrate to which the pattern is to be transferred, and cures the imprint resist by irradiating light to the imprint resist while setting the template close to the substrate to which the pattern is to be transferred, via the imprint resist. In the first embodiment, that the inspection-image acquisition mechanism 10 performs a imprint process and an imaging process of a defect inspection image is explained. However, the inspection-image acquisition mechanism 10 can perform only an imaging process of a defect inspection image.

The inspection-image acquisition mechanism 10 according to the first embodiment is configured to include an imaging device capturing an image, and captures a defect inspection image of a template by irradiating light to the template while contacting the template to a substrate (hereinafter, "resist-sandwiching substrate") used for defect inspection via a colored resist. Specifically, a pattern surface (a pattern-formed surface) of the template is contacted to a colored resist coated on the resist-sandwiching substrate. After the colored resist is filled into a fine pattern of the template, defect inspection of the template is performed. The defect inspection is performed by irradiating light such as ultraviolet (UV) rays or KrF from a back surface of the template, and by using a transmission light or a reflection light of this light, for example.

The colored resist has an optical constant determined based on optical constants (reflectance ratio and absorption rate) of the template and the resist-sandwiching substrate. The colored resist is a fluid (liquid or the like) having predetermined viscosity, and is confined into a gap between the template and the resist-sandwiching substrate. The colored resist can be a imprint resist used for the imprint, or can be a fluid other than the imprint resist. A defect inspection image captured by the inspection-image acquisition mechanism 10 is transmitted to the inspection-image processing mechanism 20.

The inspection-image processing mechanism 20 is configured to include an image processing apparatus that performs various image processes to the defect inspection image. The inspection-image processing mechanism 20 performs an image process to the defect inspection image to make it possible to recognize the distinction between a defect present in the template and the template. The inspection-image processing mechanism 20 analyzes a defect of the template based on the defect inspection image. Specifically, the inspection-image processing mechanism 20 specifies a position of the defect on the template based on the defect inspection image, and transmits the specified position information to the template cleaning mechanism 30.

The template cleaning mechanism 30 cleans the template used in the inspection-image acquisition mechanism 10. When position information of a defect is received from the inspection-image processing mechanism 20, the template cleaning mechanism 30 cleans the template based on this position information.

The template station 40 is an apparatus that stores the template, and takes the template out to the inspection-image acquisition mechanism 10 and the template cleaning mechanism 30, and takes the template in from the inspection-image acquisition mechanism 10 and the template cleaning mechanism 30. The template station 40 stores the template before performing the imprint, the defect inspection, and the cleaning, and stores the template after performing the imprint, the defect inspection, and the cleaning.

The wafer station 50 takes a wafer into the template inspection apparatus 1, and takes a wafer out from the template inspection apparatus 1. The wafer that the wafer station 50 takes out and takes in can be a wafer used for imprint or can be a resist-sandwiching substrate.

Figure 2:
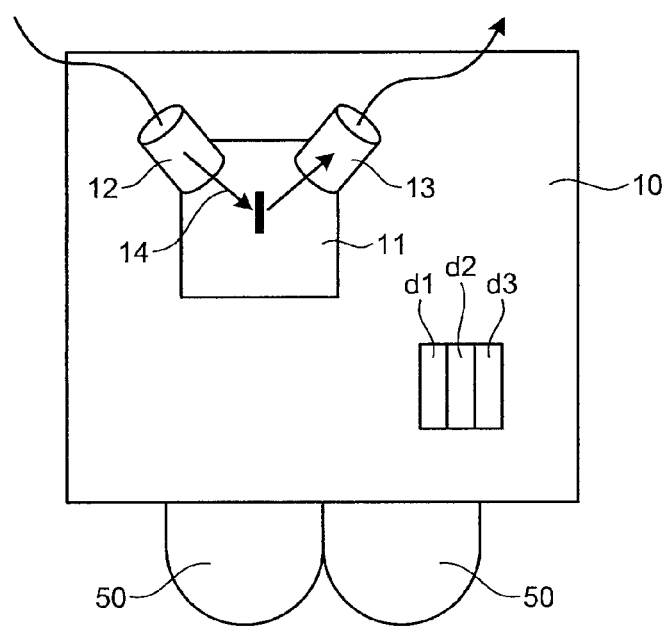
FIG. 2 is a configuration diagram of an inspection-image acquisition mechanism.

FIG. 2 is a configuration diagram of the inspection-image acquisition mechanism. The inspection-image acquisition mechanism 10 includes a template arrangement table 11, a light irradiating unit (inspection light source) 12, a light receiving unit (inspection-image detecting unit) 13, and dispensers d1 to d3. The template arrangement table 11 is a table on which the template and the like are mounted. At the time of performing defect inspection of the template, the template and the resist-sandwiching substrate are mounted on the template arrangement table 11 in a state that the template and the resist-sandwiching substrate are contacted to each other via the colored resist. The template and the resist-sandwiching substrate are mounted on the template arrangement table 11 in such a manner that the resist-sandwiching substrate becomes at a lower surface side and the template becomes at an upper surface side.

The light irradiating unit 12 irradiates light 14 used for the imprint and the defect inspection, to the template. The light receiving unit 13 detects and receives light reflected from the template and the resist-sandwiching substrate or light transmitted through the template and the resist-sandwiching substrate after being emitted from the light irradiating unit 12. The light received by the light receiving unit 13 is transmitted to the inspection-image processing mechanism 20.

FIG. 2 depicts a state that both the light irradiating unit 12 and the light receiving unit 13 are arranged at an upper surface side of the template arrangement table 11 (reflection inspection mode described later). When defect inspection is performed in a transmission inspection mode described later, the light irradiating unit 12 is arranged at the upper surface side of the template arrangement table 11, and the light receiving unit 13 is arranged at the lower surface side of the template arrangement table 11.

The dispensers d1 to d3 are apparatus that discharge the imprint resist and the colored resist by a predetermined quantity. For example, the imprint resist is discharged from the dispenser d1 onto the substrate to which a pattern is transferred such as the wafer. A first colored resist is discharged from the dispenser d2 onto the resist-sandwiching substrate. A second colored resist is discharged from the dispenser d3 onto the resist-sandwiching substrate.

A defect-inspection processing method of a template (a imprint defect-inspection process) is explained next. A defect inspection method of a template includes a method of performing defect inspection of a template by using light transmitted through a template and a colored resist (transmission inspection mode), and a method of performing defect inspection of a template by using light reflected from an interface between the template and the colored resist or an interface (colored resist surface) between the colored resist and the resist-sandwiching substrate (reflection inspection mode).

Figure 3:
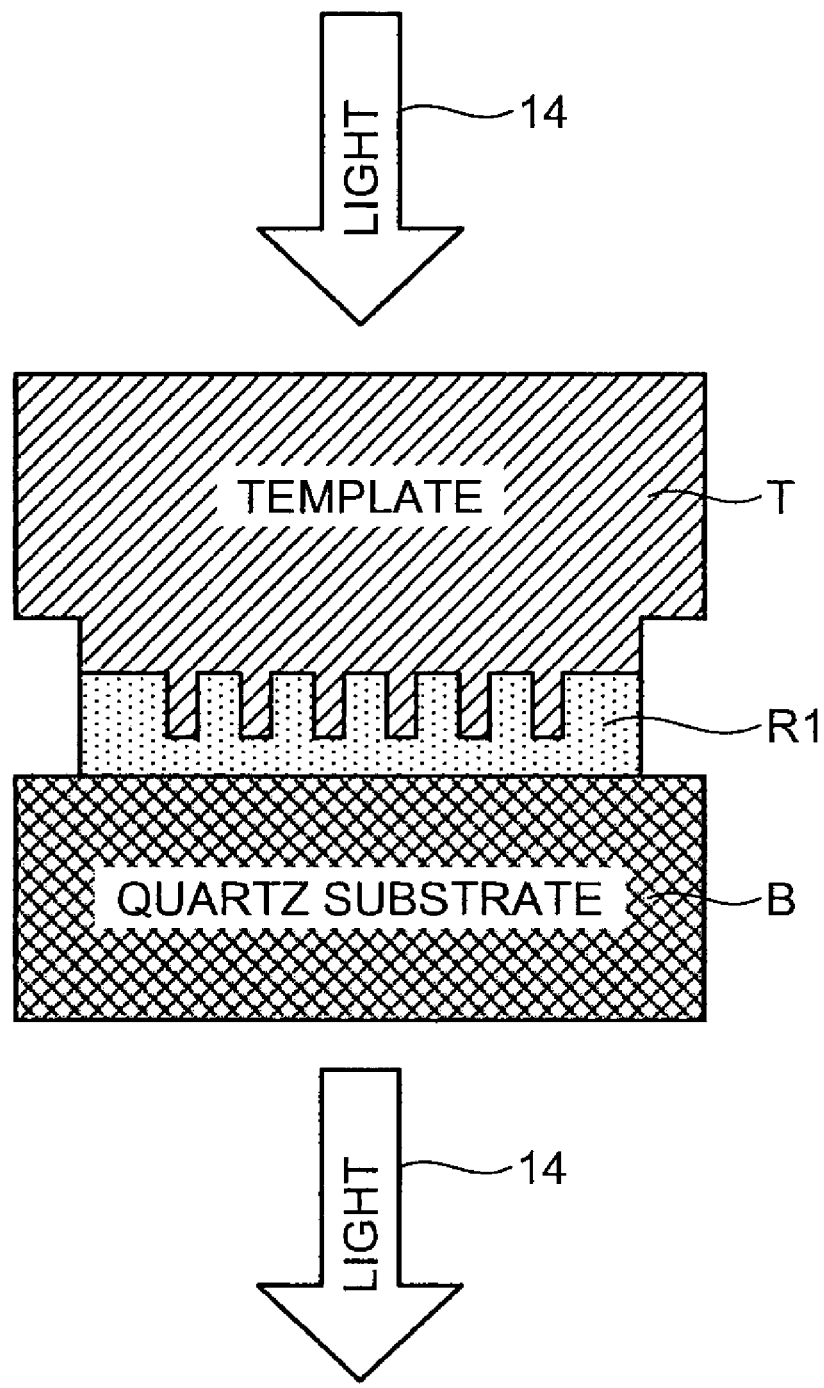
FIG. 3 is a schematic diagram for explaining a defect inspection method in a transmission inspection mode.

FIG. 3 is a schematic diagram for explaining a defect inspection method in the transmission inspection mode. FIG. 3 is a cross-sectional view of a template T and the like. In the defect inspection method in the transmission inspection mode, a transparent substrate such as a quartz substrate B is used for the resist-sandwiching substrate. To perform defect inspection of the template T, a colored resist R1 is first coated onto the quartz substrate B which is flat and transparent. The colored resist R1 is discharged from the dispenser d2, for example, and is coated onto the quartz substrate B from a nozzle (not shown). The colored resist R1 is a fluid having low viscosity (for example, 5 centipoises (cp)) and having sufficiently high liquidity. Thereafter, the inspection-image acquisition mechanism 10 sets the template T close to the quartz substrate B. When the colored resist R1 is contacted to a surface of the template T, the colored resist R1 is filled into a fine pattern of the template T based on capillary action.

After the colored resist R1 is sufficiently filled, the inspection-image acquisition mechanism 10 applies the light 14 from a back surface of the template T (main surface at the opposite side of a pattern formation surface which is set close to the colored resist R1), and observes a transmission light of this light (the light 14) at a back surface of the quartz substrate B (main surface at the opposite side of the colored resist R1), thereby performing defect inspection. Specifically, the light irradiating unit 12 irradiates the light 14 to the template T. The light 14 from the light irradiating unit 12 is transmitted through the template T, the resist R1, and the quartz substrate B. The light receiving unit 13 receives the light 14 transmitted through the template T and the like, and transmits this light to the inspection-image processing mechanism 20 as an inspection signal. The inspection-image processing mechanism 20 extracts a defect portion.

Figure 4:
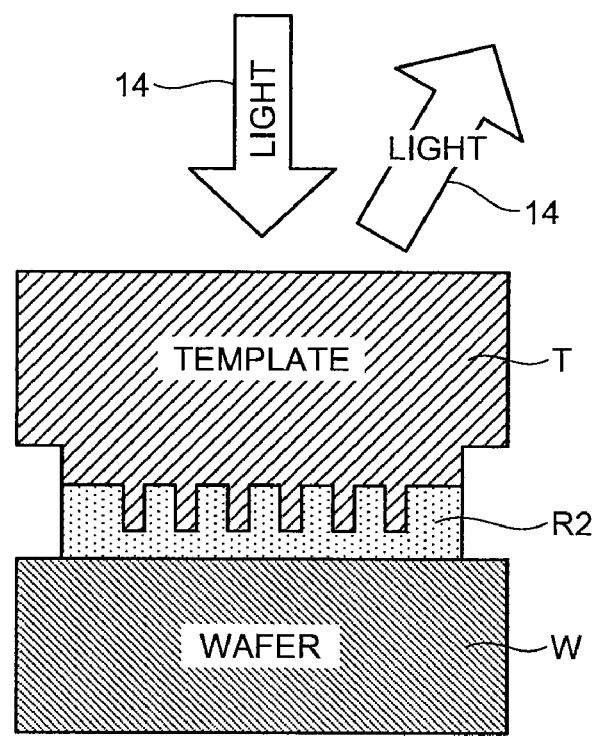
FIG. 4 is a schematic diagram for explaining a defect inspection method in a reflection inspection mode.

FIG. 4 is a schematic diagram for explaining a defect inspection method in the reflection inspection mode. FIG. 4 is a cross-sectional view of the template T and the like. In the defect inspection method in the reflection inspection mode, an opaque wafer W (such as a silicon substrate) is used for the resist-sandwiching substrate. The defect inspection method in the reflection inspection mode is substantially the same as the defect inspection method in the transmission inspection mode, except that a light path of the light 14 at the defect inspection time is different. To perform defect inspection of the template T, a colored resist R2 is first coated onto the wafer W which is flat. The colored resist R2 is discharged from the dispenser d3, and is coated onto the wafer W from a nozzle (not shown). The colored resist R2 is a resist similar to that of the resist R1, and is a fluid having low viscosity and high liquidity. Thereafter, the inspection-image acquisition mechanism 10 sets the template T close to the wafer W. When the colored resist R2 is contacted to the surface of the template T, the colored resist R2 is filled into a fine pattern of the template T based on capillary action.

After the colored resist R2 is sufficiently filled, the inspection-image acquisition mechanism 10 applies the light 14 from the back surface of the template T, and observes a transmission light of this light at a back surface of the template T, thereby performing defect inspection. Specifically, the light irradiating unit 12 irradiates the light to the template T. The light 14 from the light irradiating unit 12 is reflected by the wafer W and the like. The light receiving unit 13 receives the light 14 reflected from the wafer W and the like, and transmits this light to the inspection-image processing mechanism 20 as an inspection signal. The inspection-image processing mechanism 20 extracts a defect portion.

The waiting time until a completion of filling the colored resists R1 and R2 is 300 seconds, for example. The colored resists R1 and R2 can be a light curing resin or the like. Optical constants of the colored resists R1 and R2 can be approximately the same as the optical constant of the template T, or can be an optical constant greatly different from that of the template T.

Figure 5:
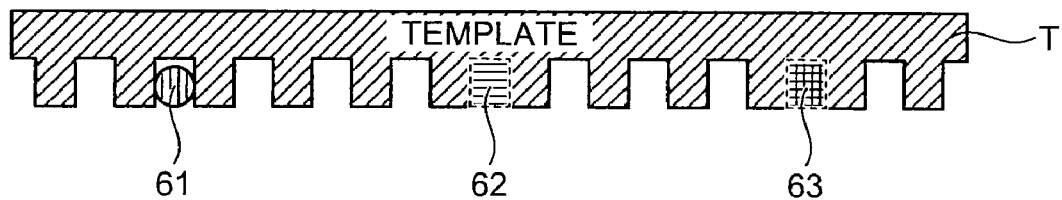
FIG. 5 is a schematic diagram for explaining types of defects on a template.

Types of defects on the template T are explained next. FIG. 5 is a schematic diagram for explaining types of defects on the template. Within gaps of a fine pattern formed on the template T, there sometimes occur a particle 61 adhered to the inside of a gap, an imprint resist remaining within a gap (clog defect) (a resist residue 62), and a template defect (holing failure in a gap) 63.

The particle 61 is a fraction generated from the imprint resist, the template T, the substrate to which a pattern is transferred, and the like. The resist residue 62 is a torn-off solidified imprint resist left in a fine gap at the side of the template T when the template T is separated from the substrate to which a pattern is transferred, after the imprint resist is solidified. The template defect 63 is a fine gap in which a hole is not actually formed among fine gaps to be formed on the template T.

Defect inspection of the template T is performed in a state that a defect such as the particle 61, the resist residue 62, and the template defect 63 is sandwiched between the template T, the resist-sandwiching substrate, and the wafer W. In the first embodiment, defect inspection of the template T is performed by using a colored resist of an optical constant corresponding to optical constants of the defect and the template T. A case that the refractive index of the template T is 1.5 is explained.

Figure 6:
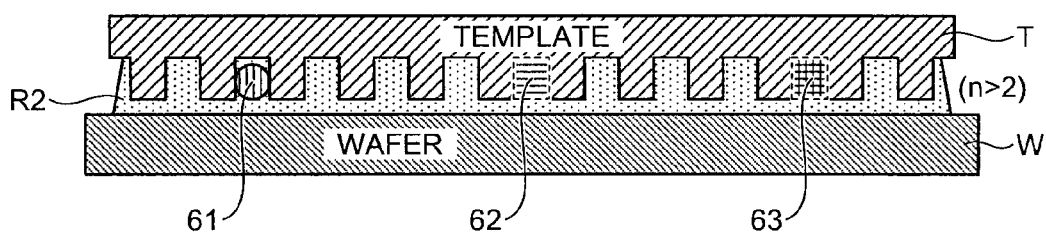
FIG. 6 is a schematic diagram for explaining a reflection inspection mode when a colored resist having a large refractive index difference from that of a template is used.

FIG. 6 is a schematic diagram for explaining the reflection inspection mode when a colored resist having a large refractive index difference from that of the template is used. When the colored resist R2 is coated onto the wafer W and also when the template T is contacted to the colored resist R2 on the wafer W, the colored resist R2 is filled between the template T and the wafer W.

For the colored resist R2, a resist having a refractive index greatly different from that of quartz as a material of the template T (for example, n>2) is used. When a reflectance ratio of the template T is 1.5 and also when a refractive index of air is 1.0, a refractive index difference between the template T and air is 0.5. In the first embodiment, the colored resist R2 having a larger refractive index difference between the template T and the colored resist R2 than the refractive index difference 0.5 is used, for example. When the colored resist R2 having a refractive index 2.5 is used, for example, a refractive index difference between the template T and the colored resist R2 becomes 1.0.

Figure 7:
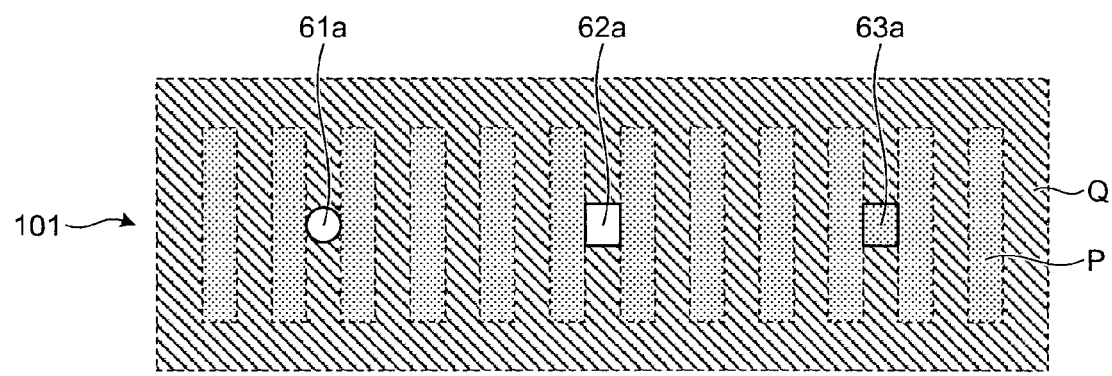
FIG. 7 depicts a defect inspection image when the colored resist having a large refractive index difference from that of the template is used.

In this case, all of the particle 61, the resist residue 62, and the template defect 63 within a defect inspection image become images of a high contrast relative to a pattern (a convex portion) of the template T. FIG. 7 depicts a defect inspection image when a colored resist having a large refractive index difference from that of the template is used. This is one example of an image captured by the inspection-image processing mechanism 20. FIG. 7 depicts a defect inspection image corresponding to the defect inspection method shown in FIG. 6.

As shown in FIG. 7, a defect inspection image (inspection optical image) 101 has an image pattern P and an image pattern Q as image patterns corresponding to patterns of the template T. The image pattern Q corresponds to the colored resist R2 filled into a gap (a concave portion) of the template T, and the image pattern P corresponds to the convex portion of the template T. When the template T has a defect, this defect also appears in the defect inspection image 101. When a refractive index difference between the template T and the colored resist R2 is large, a large difference of brightness occurs between the image pattern P and the image pattern Q.

In FIG. 7, the image of the particle 61, the image of the resist residue 62, and the image of the template defect 63 appear as an image 61a, an image 62a, and an image 63a, respectively in the defect inspection image 101. When the particle 61, the resist residue 62, and the template defect 63 are present in the gaps of the template T, the colored resist R2 does not permeate these defect portions.

The particle 61 and the resist residue 62 have own refractive indexes different from those of the template T and the colored resist R2. Further, in this case, the colored resist R2 having a larger contrast between the image pattern P and the image pattern Q is used. Therefore, the image 61a of the particle 61 and the image 62a of the resist residue 62 have strong contrast to both the image pattern P and the image pattern Q. Consequently, the particle 61 and the resist residue 62 can be distinctly detected from the template T and the colored resist R.

On the other hand, the template defect 63 has a refractive index similar to that of the template T. Therefore, the template defect 63 becomes an image having brightness similar to that of a portion (the image pattern P) where the colored resist R2 is not present. In other words, the template defect 63 becomes an image having a large brightness difference from the concave portion (the image pattern Q) of the template T.

In this way, by using the colored resist R2 making a large refractive index difference between the template T and the colored resist R2, defects on the template T can be easily extracted.

Figure 8:
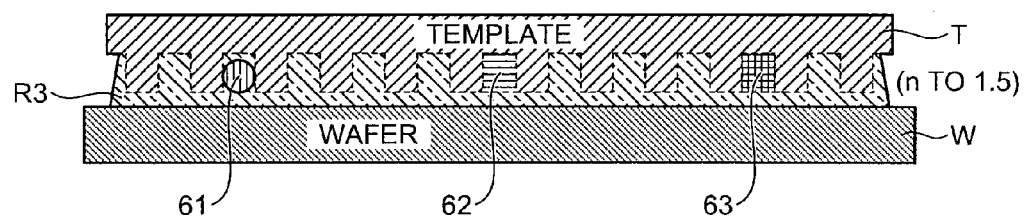
FIG. 8 is a schematic diagram for explaining a reflection inspection mode when a colored resist having approximately the same refractive index as that of the template is used.

As for the colored resist, a resist of which refractive index is approximately the same as that of the quartz as a material of the template T (n to 1.5) can be used. FIG. 8 is a schematic diagram for explaining the reflection inspection mode when a colored resist having approximately the same refractive index as that of the template is used. When the colored resist R3 is coated onto the wafer W and also when the template T is contacted to the colored resist R3 on the wafer W, the colored resist R3 is filled between the template T and the wafer W. The colored resist R3 is a fluid similar to the colored resists R1 and R2, and has an optical constant different from those of the colored resists R1 and R2.

In the first embodiment, for the colored resist R3, a resist of which refractive index is approximately the same as that of the quartz as a material of the template T (n to 1.5) is used, for example. When a reflectance ratio of the template T is 1.5 and also when a refractive index of air is 1.0, a refractive index difference between the template T and air is 0.5. On the other hand, when a refractive index of the colored resist R3 is approximately the same as the refractive index of the template T, a refractive index difference between the template T and the colored resist R2 becomes approximately zero.

Figure 9:
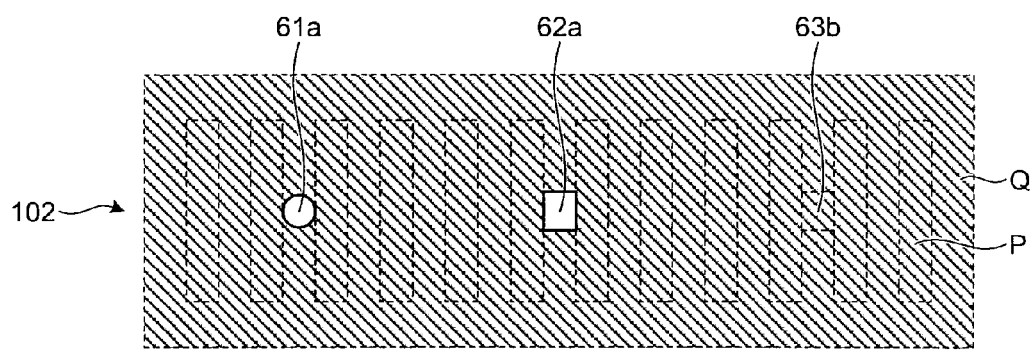
FIG. 9 depicts a defect inspection image when the colored resist having approximately the same refractive index as that of the template is used.

In this case, the particle 61 and the resist residue 62 as defect inspection images become images of a high contrast relative to a pattern (a convex portion) of the template T. FIG. 9 depicts a defect inspection image when a colored resist having the same refractive index as that of the template is used. This is one example of an image captured by the inspection-image processing mechanism 20. FIG. 9 depicts a defect inspection image corresponding to the defect inspection method shown in FIG. 8.

As shown in FIG. 9, a defect inspection image 102 has the image pattern P and the image pattern Q in a similar manner to that of the defect inspection image 101. The image pattern Q corresponds to the colored resist R3 filled into a gap of the template T, and the image pattern P corresponds to the convex portion of the template T. When the template T has a defect, this defect also appears in the defect inspection image 102. When a refractive index of the template T and a refractive index of the colored resist R3 are the same, the image pattern P and the image pattern Q have the same brightness.

When the particle 61, the resist residue 62, and the template defect 63 are present in the gaps of the template T, the colored resist R3 does not permeate these defect portions. The template defect 63 has the same refractive index as those of the template T and the colored resist R3. Therefore, the image of the template defect 63 has the same brightness as that of the image pattern P and the image pattern Q, among defect portions of the template T. On the other hand, among the defect portions of the template T, the images of the particle 61 and the resist residue 62 have a large brightness difference from the image pattern P and the image pattern Q.

As explained above, when a refractive index of the template T and a refractive index of the colored resist R3 are the same, contrast of concave and convex patterns of the template T and the template defect 63 of the template T becomes low, and detection becomes difficult. On the other hand, the particle 61 and the resist residue 62 can be detected in high contrast. In this way, by using the colored resist R3, only the particle 61 adhered to the template T and the resist residue 62 are displayed with emphasis, and defect detection efficiency is improved. As a result, extremely fine defects of the template T can be detected in high sensitivity.

Further, by performing the reflection inspection explained with reference to FIG. 6 and FIG. 8 to the same template T and by comparing the defect inspection image (first inspection image) 101 as an inspection image of the reflection inspection with the defect inspection image (second inspection image) 102, template defects can be detected while distinguishing the types of defects. Therefore, by using the colored resist R3 having approximately the same refractive index as that of the template T, only predetermined defects (the particle 61, the resist residue 62) out of the defects on the template T can be easily extracted.

Figure 10:
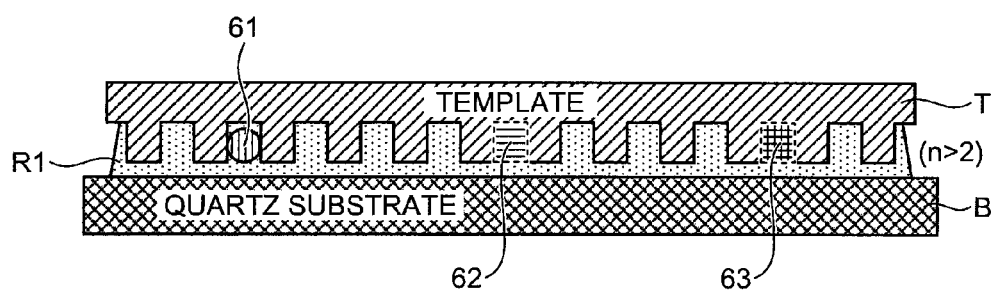
FIG. 10 is a schematic diagram for explaining a transmission inspection mode when a colored resist having a large refractive index difference from that of the template is used.

Defect inspection when a refractive index difference between the template T and the colored resist R1 is increased can be applied to the transmission inspection mode. FIG. 10 is a schematic diagram for explaining the transmission inspection mode when a colored resist having a large refractive index difference from the template is used. When the colored resist R1 is coated onto the quartz substrate B and also when the template T is contacted to the colored resist R1 on the quartz substrate B, the colored resist R1 is filled between the template T and the quartz substrate B.

When defect inspection of the template T is performed in this state, a defect inspection image similar to the defect inspection image 101 shown in FIG. 7 is acquired. Therefore, when defect inspection is performed in the transmission inspection mode by using the colored resist R1 having a large refractive index difference from the template T, defects on the template T can be also easily extracted in a similar manner to that when defect inspection is performed in the reflection inspection mode by using the colored resist R1.

Figure 11:
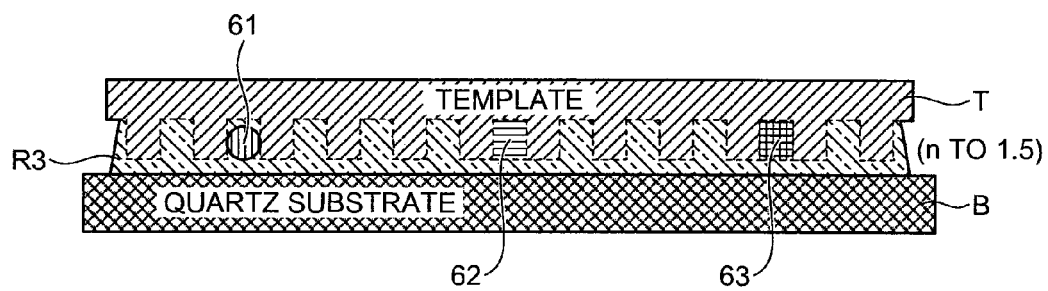
FIG. 11 is a schematic diagram for explaining a transmission inspection mode when the colored resist having approximately the same refractive index as that of the template is used.

Further, defect inspection when a refractive index of the template T is set the same as a refractive index of the colored resist R3 can be applied to the transmission inspection mode. FIG. 11 is a schematic diagram for explaining the transmission inspection mode when a colored resist having the same refractive index as that of the template is used. When the colored resist R3 is coated onto the quartz substrate B and also when the template T is contacted to the colored resist R1 on the quartz substrate B, the colored resist R3 is filled between the template T and the quartz substrate B.

When defect inspection of the template T is performed in this state, a defect inspection image similar to the defect inspection image 102 shown in FIG. 9 is acquired. Therefore, when defect inspection is performed in the transmission inspection mode by using the colored resist R3 having a refractive index approximately the same as that of the template T, predetermined defects on the template T can be also easily extracted in a similar manner to that when defect inspection is performed in the reflection inspection mode by using the colored resist R3.

After the defect inspection of the template T is performed, the template cleaning mechanism 30 cleans the template T which is inspected by the inspection-image acquisition mechanism 10. The template cleaning mechanism 30 receives position information of a defect from the inspection-image processing mechanism 20, and cleans the template T based on this position information. The imprint is then performed by using the cleaned template T having no defect. This forms a pattern on the substrate and then a semiconductor device is manufactured.

In the first embodiment, while defect inspection of the template T is performed by using the colored resist R3 having the same optical constant as that of the template T (the template defect 63), a colored resist having the same optical constant as those of the particle 61 and the resist residue 62 can be also used. When a colored resist X1 (not shown) having the same optical constant as that of the particle 61 is used, defects other than the particle 61 can be easily extracted. When a colored resist X2 (not shown) having the same optical constant as that of the resist residue 62 is used, defects other than the resist residue 62 can be easily extracted. Further, by comparing defect inspection images when these colored resists X1, X2, and R3 are used, defect inspection can be performed while distinguishing between the particle 61, the resist residue 62, and the template defect 63.

In the first embodiment, while performing defect inspection of the template T is explained, defect inspection of a phase shift mask (photomask having a concave and a convex generated by etching quartz) can be also performed.

In the first embodiment, while performing defect inspection of the template T without solidifying the colored resists R1 to R3 has been explained, defect inspection of the template T can be performed after solidifying the colored resists R1 to R3. In performing defect inspection of the template T without solidifying the colored resists R1 to R3, the defect inspection of the template T is performed by the light 14 of a wavelength generating no solidification of the colored resists R1 to R3. In performing defect inspection of the template T after solidifying the colored resists R1 to R3, the colored resists R1 to R3 having large optical constants after the solidification or having the same optical constant as that of the template T are used.

In performing defect inspection of the template T after solidifying the colored resists R1 to R3, defect inspection images can be captured after solidifying the colored resists R1 to R3 at two times at different positions (different resist-sandwiching substrates or different shots). With this arrangement, it can be determined whether defects appearing in the defect inspection images are defects attributable to a resist-sandwiching substrate or defects attributable to the template T. For example, when the same defect is present at the same position (the same position within a shot) of two defect inspection images, it can be determined that the defect is attributable to the template T. On the other hand, when a defect is present in only one of two defect inspection images, it can be determined that the defect is attributable to a resist-sandwiching substrate. Further, defect inspection of a resist-sandwiching substrate can be performed by capturing a defect inspection image by using the template T which is confirmed to have no defect.

In the first embodiment, while a case of inputting the light 14 from the back surface side of the template T in performing defect inspection in the transmission inspection mode has been explained, the light 14 can be input from the back surface side of the quartz substrate B.

Further, among defects appearing in the defect inspection image, only a defect which becomes a processing defect at the time of performing a imprint process can be extracted. In this case, the inspection-image processing mechanism 20 determines and extracts a defect which becomes a imprint processing defect, based on a size and a position of a defect appearing in the defect inspection image.

As explained above, defect inspection is performed by using the colored resists R1 to R3 determined based on optical constants of the template T and the resist-sandwiching substrate. Therefore, even when the template T is transparent quartz, optical inspection of the template T can be easily performed. Further, even when the template T is a template of the same magnification and when a size of a defect to be detected is small, defect inspection of the template T can be easily performed.

As explained above, according to the first embodiment, the colored resists R1 and R2 of which refractive index differences from the template T are large are sandwiched between the template T and the resist-sandwiching substrate, thereby performing defect inspection of the template T. Therefore, high-precision defect inspection of the template T can be performed easily.

Because defect inspection of the template T is performed by sandwiching the colored resist R3 having the same refractive index as that of the template T between the template T and the resist-sandwiching substrate, defects other than the template defect 63 can be easily extracted.

Because defect inspection images are captured by using at least two kinds of the colored resists R1 to R3 having different optical constants and the captured defect inspection images are compared, defects can be detected while distinguishing the types of defects.

A second embodiment of the present invention is explained next with reference to FIG. 12. In the second embodiment, a conductive light-curing resin (a conductive light curing material) is sandwiched between the template T and the resist-sandwiching substrate, and the conductive light-curing resin is hardened. The template T is then separated from the conductive light-curing resin, and the conductive light-curing resin is inspected by EB (electron beam) inspection.

For the template inspection apparatus 1, the template inspection apparatus 1 explained in the first embodiment is used. In the template inspection apparatus 1 according to the second embodiment, the light irradiating unit 12 irradiates an EB. The template inspection apparatus 1 in this case includes an EB detecting unit 72 instead of the light receiving unit 13, and the EB detecting unit 72 detects a reflection EB. In the second embodiment, the colored resists R2 and R3 are used, and defect inspection of the template T is performed by using a defect inspection method in the reflection inspection mode.

Figure 12:
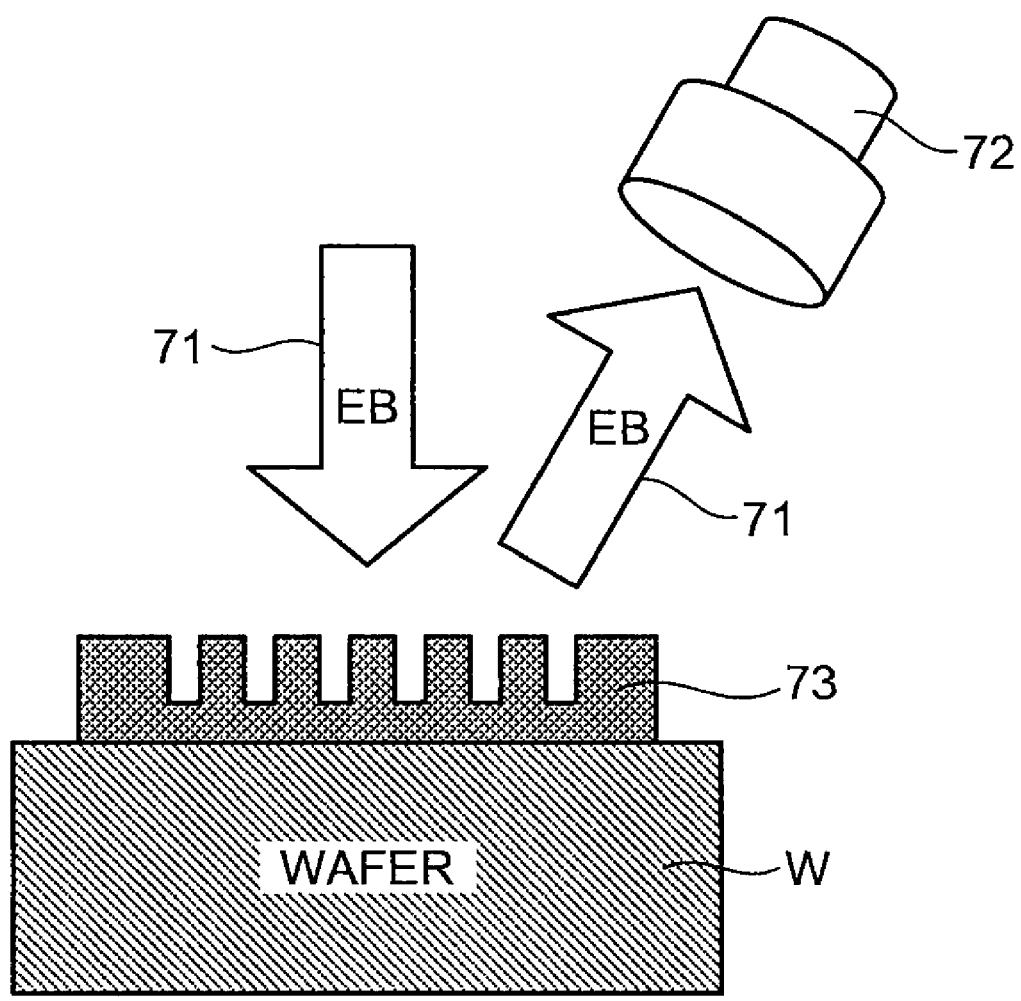
FIG. 12 is a schematic diagram for explaining a defect inspection method in a reflection inspection mode according to a second embodiment of the present invention.

FIG. 12 is a schematic diagram for explaining the defect inspection method in the reflection inspection mode according to the second embodiment. FIG. 12 is a cross-sectional view of the wafer W and the like. To perform defect inspection of the template T, the wafer W (semiconductor substrate or the like) and the template T are prepared. An imprint resist (a conductive light-curing resin 73) configured by including a resin having conductivity and a light curing characteristic is coated onto the wafer W. The conductive light-curing resin 73 is discharged from the dispenser d2 and the dispenser d3, and is coated onto the wafer W.

For the conductive light-curing resin 73 used in the second embodiment, CONISOL U-200 (polythiophene conductive polymer+acrylic monomer) and the like can be mentioned. After the conductive light-curing resin 73 is coated onto the wafer W, the template T is contacted to the conductive light-curing resin 73, and this state is left as it is until when the conductive light-curing resin 73 is completely filled into the template T.

When the conductive light-curing resin 73 is contacted to the surface of the template T, the conductive light-curing resin 73 is filled into a fine pattern of the template T based on capillary action. After the conductive light-curing resin 73 is sufficiently filled, the inspection-image acquisition mechanism 10 applies the light 14 such as UV rays from the back surface of the template T, thereby hardening the conductive light-curing resin 73. Thereafter, the template T is separated from the conductive light-curing resin 73, and the hardened conductive light-curing resin 73 is demolded from the template T.

The template inspection apparatus 1 performs EB inspection (electron beam observation) of a template pattern (replica image) (transfer pattern) by the conductive light-curing resin 73 formed in this way. Specifically, the light irradiating unit 12 irradiates EB 71 to the hardened conductive light-curing resin 73. When the EB 71 is irradiated to the conductive light-curing resin 73, the EB 71 is reflected by the conductive light-curing resin 73 and the like. The EB detecting unit 72 receives the EB 71 reflected by the conductive light-curing resin 73 and the like, and transmits the EB 71 to the inspection-image processing mechanism 20 as an inspection signal. The inspection-image processing mechanism 20 extracts a defect portion.

In the second embodiment, while the polythiophene conductive polymer+acrylic monomer is used for the conductive light-curing resin 73 to perform the EB inspection of a template pattern, other conductive light-curing resin can be also used. In the second embodiment, while the use of the conductive light-curing resin 73 has been explained, a material other than a resin can be also used for the defect inspection of the template T. In the second embodiment, while the inspection of a conductive light-curing resin by EB has been explained, the conductive light-curing resin can be inspected also by optical inspection.

As explained above, because defect inspection of the template T is performed by using a conductive light-curing resin, defect inspection of the template T using EB can be easily performed even when the template T is an insulator.

As explained above, according to the second embodiment, a transfer pattern of the template T is generated by using a conductive light-curing resin, and electron beam observation of the transfer pattern is performed by EB. Therefore, a high-precision defect inspection of the template T can be easily performed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A template inspection method for performing defect inspection of a template, by bringing a pattern formation surface of a template used to form a pattern close to a first fluid coated on a flat substrate, filling the first fluid into a pattern of the template, and by performing optical observation of the template in a state that the first fluid is sandwiched between the template and the substrate, wherein
   a difference between an optical constant of the first fluid and an optical constant of the template is larger than a difference between an optical constant of air and the optical constant of the template.

2. The template inspection method according to claim 1, wherein defect inspection of the template is performed by optically observing light transmitted through the template and the first fluid.

3. The template inspection method according to claim 1, wherein defect inspection of the template is performed by optically observing light reflected from at least one of an interface between the template and the first fluid and an interface between the first fluid and the substrate.

4. The template inspection method according to claim 1, wherein
   the first fluid has a first optical constant, and
   defect inspection of the template is performed by comparing a first inspection image optically observed in the state that the first fluid is sandwiched between the template and the substrate with a second inspection image optically observed in a state that a second fluid having a second optical constant is sandwiched between the template and the substrate.

5. The template inspection method according to claim 4, wherein the second optical constant is the same as the optical constant of the template.

6. The template inspection method according to claim 1, wherein
   the first fluid is a light-curing resin, and
   a difference between an optical constant of the first fluid and an optical constant of the template after solidification of the light-curing resin is larger than a difference between an optical constant of the template and an optical constant of the air.

7. The template inspection method according to claim 1, wherein defect inspection of the template is performed by comparing inspection images optically observed on different substrates or at different shot positions on the template.

8. The template inspection method according to claim 1, wherein defect inspection of the template is performed by using a template which is confirmed to have no defect.

* * * * *